US 6,694,185 B2

(12) United States Patent
Orton

(10) Patent No.: US 6,694,185 B2
(45) Date of Patent: Feb. 17, 2004

(54) APPARATUS AND METHOD FOR ELECTRICALLY CONDUCTIVE WEIGHT REDUCTION

(76) Inventor: Kevin R. Orton, 257 Avenida Lobeiro Unit G, San Clemente, CA (US) 92672

( * ) Notice: Subject to any disclaimer, the term of this patent is extended or adjusted under 35 U.S.C. 154(b) by 0 days.

(21) Appl. No.: 10/215,871

(22) Filed: Aug. 8, 2002

(65) Prior Publication Data

US 2003/0032985 A1 Feb. 13, 2003

Related U.S. Application Data

(60) Provisional application No. 60/311,031, filed on Aug. 8, 2001.

(51) Int. Cl.$^7$ ................................................. F61N 1/18
(52) U.S. Cl. ........................... 607/2; 128/898; 607/149
(58) Field of Search ................. 607/2, 40–42, 607/46, 48, 72–75, 142–144, 148, 149, 152–153; 128/898

(56) References Cited

U.S. PATENT DOCUMENTS

| 4,485,805 | A | | 12/1984 | Foster, Jr. | |
|---|---|---|---|---|---|
| 4,592,342 | A | | 6/1986 | Salmasian | |
| 4,722,354 | A | * | 2/1988 | Axelgaard et al. | 607/152 |
| 4,946,453 | A | | 8/1990 | Monson | |
| 4,952,913 | A | | 8/1990 | Pauley et al. | |
| 5,073,984 | A | | 12/1991 | Tone et al. | |
| 5,109,846 | A | * | 5/1992 | Thomas | 607/115 |
| D337,419 | S | | 7/1993 | Oper | |
| 5,453,270 | A | | 9/1995 | Bills | |
| 5,575,809 | A | * | 11/1996 | Sasaki | 607/62 |
| 5,700,231 | A | | 12/1997 | Wilkinson | |
| 5,906,004 | A | | 5/1999 | Lebby et al. | |
| 5,913,836 | A | * | 6/1999 | Groux | 601/21 |
| 5,935,882 | A | | 8/1999 | Fujita et al. | |
| 5,985,282 | A | | 11/1999 | Haveson | |
| 5,989,574 | A | | 11/1999 | Slavin | |
| 6,065,154 | A | | 5/2000 | Hulings et al. | |
| 6,080,690 | A | | 6/2000 | Lebby et al. | |
| 6,097,297 | A | | 8/2000 | Fard | |
| 6,191,117 | B1 | | 2/2001 | Kozachuk | |
| 6,204,291 | B1 | | 3/2001 | Sunvold et al. | |

FOREIGN PATENT DOCUMENTS

| EP | 0788811 A1 | 8/1997 |
|---|---|---|
| EP | 1027907 A1 | 8/2000 |
| FR | 2758268 A1 | 7/1998 |
| WO | WO 01/2052 | 1/2001 |
| WO | WO 01/26641 | 4/2001 |

OTHER PUBLICATIONS

Market Inc. (website) pp. 1–2, http://www.market-inc.com/rpoducts.htm.

* cited by examiner

Primary Examiner—Jeffrey R. Jastrzab
(74) Attorney, Agent, or Firm—Orrick, Herrington & Sutcliffe LLP

(57) ABSTRACT

An apparatus that aids in the loss of weight through the reduction of fatty body tissues. The apparatus is preferably in a garment configuration, provides electrically conducting portions and insulating portions configured in such a way that the potential of electrochemical signal messaging system in the patient's body is altered. The re-directed currents trigger a release of stored fatty tissues, and a reduction of weight. The electrically conductive portions are configured and provided in a manner that permits safe and effective use. The device may be sold and marketed as a weight reduction or muscle building apparatus.

30 Claims, 2 Drawing Sheets

APPARATUS AND METHOD FOR ELECTRICALLY CONDUCTIVE WEIGHT REDUCTION

This application claims benefit of Provisional application No. 60/311,031, filed Aug. 8, 2001.

FIELD OF THE INVENTION

The field of the invention relates to treatment of medical conditions in a patient, and more particularly to reducing weight through use of electrical conductivity within the patient.

BACKGROUND

Obesity is a problem that afflicts a large number of people. Some people are unable to lose weight in specific areas, while others have a general weight control problem. Others do not wish to expend the time and energy required for vigorous exercise. Various existing weight reduction methods include such things as calorie intake reduction, exercise, herb teas, stimulant drugs, liposuction, grapefruit plans, etc. However, for many people, existing methods either are too costly, difficult, or simply do not provide the results desired.

For example, many people are incapable of sticking to a diet or exercise plan. Many people are unable or unwilling to limit their food consumption either in quantity or in quality. Additionally, many people are reluctant to undergo surgical procedures to reduce weight, and/or are reluctant to take weight control medications, because of the potential complications or other undesirable effects. Thus it is desirable to provide an effective alternative for losing weight for people for whom existing methods are not satisfactory.

SUMMARY OF THE INVENTION

In an embodiment of the invention, a method is provided of effective weight loss with a novel bio-electro-chemical action means. An embodiment offers a new and improved method of weight loss, one that is simple to administer and easy for the user to follow. An embodiment achieves weight reduction that may be difficult or impossible to obtain with other methods. An embodiment operates on a molecular level to dislodge fat molecules and cause them to enter the bloodstream, where they may be metabolized away. In an embodiment, electric current flow is induced in the patient to dislodge fat molecules. In an embodiment, a novel means of metabolic activity is provided in such a way as to allow reduction of previously difficult to metabolize tissue. An embodiment requires minimal user effort, making it easy for the user to obtain results.

BRIEF DESCRIPTION OF THE DRAWINGS

The accompanying drawings are included to provide a further understanding of embodiments of the invention and together with the Detailed Description, serve to explain the principles of the embodiments disclosed.

DETAILED DESCRIPTION OF THE PREFERRED EMBODIMENTS

Overview of the Garment

Figure 1:
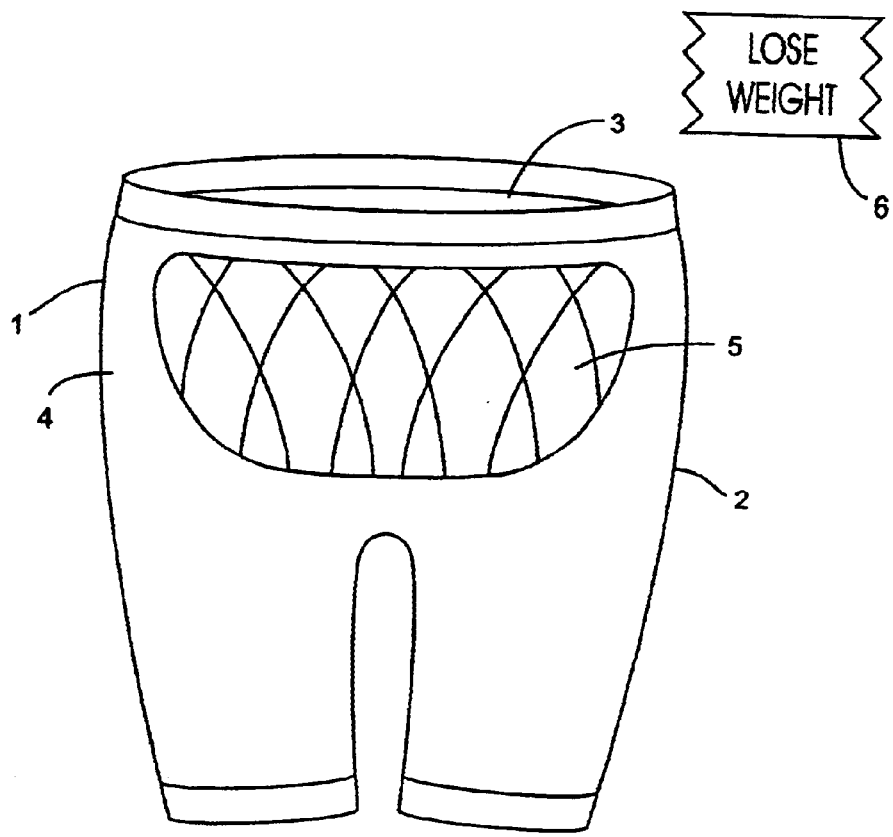
FIGS. 1 and 2 show a weight control garment with electrically conductive portions, in accordance with an embodiment of the invention.

Turning to FIG. 1, a garment 1 in accordance with an embodiment of the invention is shown. The garment 1 is adapted to be worn by a patient seeking to lose weight. In the embodiment of FIG. 1, the garment 1 is a pair of pants. In other embodiments, the garment 1 can be any other form of garment useful to facilitate weight reduction in accordance with the principles disclosed below, such as a shirt, an armpad, a kneepad, a girdle, leggings, or other similar items.

The garment 1 is constructed of a flexible material 2, such as cloth, plastic, paper, or other materials suitable for use in constructing garments. The flexible material 2 is preferably composed of an elastic material, such that the garment 1 fits snugly around the body of the patient. The garment 1 includes an inner surface 3 and an outer surface 4. The inner surface 3 is adapted to be in contact with a wearer of the garment. Attached to the inner surface 3 are one or more pieces of a flexible, electrically-conductive material 5. The flexible, electrically-conductive material portions 5 may be mounted inside the garment 2 using glues, seams, snaps, or other such fasteners adapted to position the flexible, electrically-conductive material portions 5 proximally to fatty deposits. The garment 1 may also include various zippers, snaps or buckles to aid in repositioning the flexible, electrically-conductive material portions 5 as desired.

The flexible, electrically-conductive material 5 may or may not be visible from the outside, depending on the particular design choice selected by those skilled in the art. The flexible, electrically-conductive material 5 generally covers one or more portions of the inner surface 3. The outer surface 4 is adapted to provide support to the inner surface 3, as well as to provide any of the other usual features found in garments, such as decoration, protection from the elements, provision of modesty, etc.

The garment 1 can be sold or merchandised in connection with an informative tag 6 that identifies the purpose of the garment 1 to a prospective customer. The informative tag 6 contains information such as "lose weight," "weight loss device," "weight loss garment," "fitness garment," "muscle toning device," "fat burning device," "device to reduce fat deposits." The informative tag 6 is adapted to enhance the marketability of the garment 1. For example, the informative tag 6 may be placed on packaging containing the garment 1, or may be used in advertising such as magazine or newspaper ads, and/or television or radio infomercials or commercials.

Figure 2:
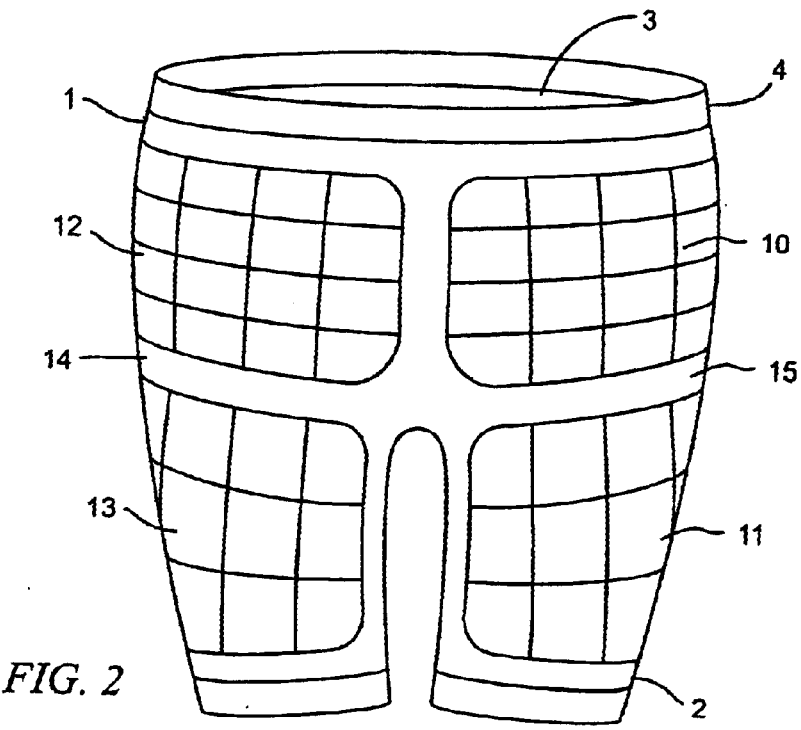

Turning to FIG. 2, the garment 1 may have multiple flexible, electrically-conductive material portions 10, 11, 12, 13. The configuration shown in FIG. 2 is adapted for the rear portion of a pair of pants to be worn by a human patient, but other configurations are also possible, for other types of garments intended for use by human or non-human patients. The garment 1 also includes several gaps 14, 15 between the flexible, electrically-conductive material portions 10, 11, 12, 13. These gaps 14, 15 are constructed of an insulating material, such that no significant electrical conduction occurs between the flexible, electrically-conductive material portions 10, 11, 12, 13 across the gaps 14, 15.

Overview of the Garment in Use

Figure 3:
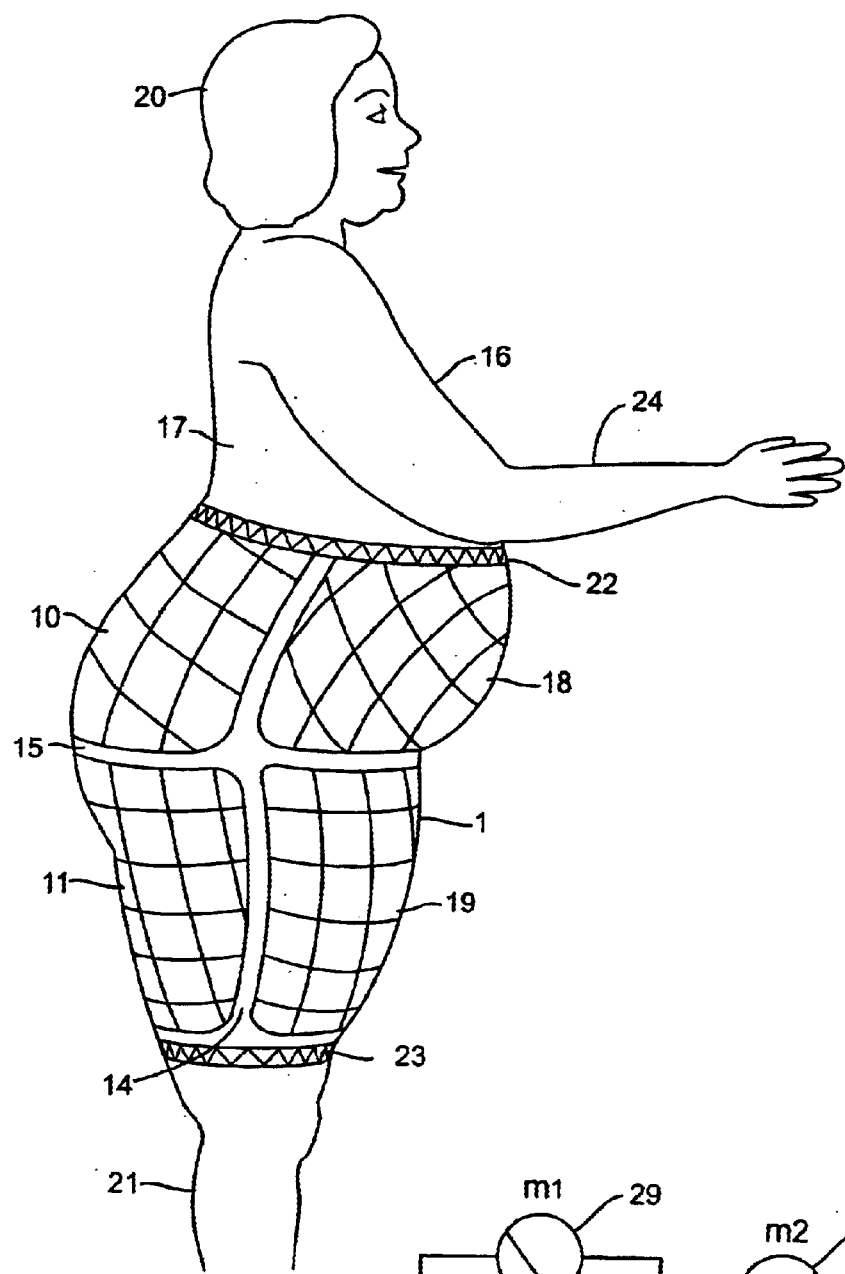
FIG. 3 shows the garment with conductive portions of FIG. 2, as worn by a patient.

Turning to FIG. 3, the garment 1 of FIG. 2 is shown as worn by a patient 16. The patient 16 includes a central portion 17, and extremities including a head 20, a leg 21, and an arm 24. Additional portions of the patient 16 are omitted for clarity. Flexible, electrically-conductive material regions 10, 11 are visible, and flexible, electrically-conductive material regions 12, 13 are obscured by the patient 16. Additionally visible in FIG. 3 are flexible, electrically-conductive material regions 18, 19, attached to the front portion of the garment 1. These flexible, electrically-conductive material portions 10, 11, 12, 13, 18, 19 are mounted on the inner surface of the garment 1, so as to be in direct contact with the skin of the patient 16. There are no insulating layers between the flexible, electrically-conductive material portions 10, 11, 12, 13, 18, 19 and the skin of the patient 16. As with the depictions of the garment 1 in FIGS. 1 and 2, the garment 1 is shown in cut-away view, to better depict the flexible, electrically-conductive material portions. In different embodiments, these portions may or may not be visible from the outside.

The flexible, electrically-conductive material portions 10 and 12 are adapted to contact the buttocks of the patient 16. The flexible, electrically-conductive material portions 11, 13, 19 are adapted to contact the thighs of the patients 16. The flexible, electrically-conductive material portion 18 is adapted to contact the abdomen of the patient 16. The garment 1 also includes an elastic waistband 22 and elastic legbands 23 to assist in maintaining contact between the flexible, electrically-conductive material portions 10, 11, 12, 13, 18, 19 and the skin of the patient 16. Other elastic elements can be used where desired to assist in maintaining contact between portions of the garment 1 and the patient 16. Additionally, the flexible, electrically-conductive material portions can be pleated, stretched, folded or formed as desired to conform to the body contours of the patient 16.

A typical flexible, electrically-conductive material portion 18, for the abdomen area of the patient 16, is approximately 12 to 24 inches wide, 10 to 20 inches high, and formed, cut or folded into a generally trapezoidal pattern with rounded corners, to conform to the typical shape of a human abdomen. The total surface area of the flexible, electrically-conductive material portion 16 ranges approximately from 0.8 to 3.3 square feet. These measurements are all dependent upon the particular characteristics of the patient 16 being treated, and will vary accordingly. Flexible, electrically-conductive material portions covering the thighs, buttocks, arms, legs and other body parts of the patient 16 are similarly fashioned.

Construction of the Electrically-Conductive Material Portions

The construction of the flexible, electrically-conductive material portions will now be discussed in more detail. These flexible, electrically-conductive material portions are formed from an electrically conductive material having a low resistance. The resistance of the conductive material is preferably approximately equal to or less than the resistance of the skin of the patient 16. This resistance is generally 10,000 ohms per square inch or less. Electrically conductive materials with resistances of 100,000 ohms per square inch or greater, such as anti-static materials, have been found to be ineffective. The flexible, electrically-conductive material portions are adapted to facilitate weight loss, and may therefore, for example, be larger and of lower resistance than other types of electrically-conductive material portions used for therapeutic purposes such as collecting readings for medical instruments, or for electrically stimulating muscles.

In a particularly preferred embodiment, the flexible, electrically-conductive material 5 is made up of silver-plated woven nylon cloth. The silver-plated nylon cloth is highly flexible, has a very low resistance, and does not irritate the skin of the patient. The whole surface of the plated cloth is readily conductive, thus allowing the maximum coverage of the skin of the patient 16 with the electrically-conductive material 5. The silver-plated nylon cloth has a resistance on the order of 1,000 ohms per square inch or less, sometime going as low as 1 ohm per square inch. Such material is commercially available, for example from Swift Textile Metalizing of Bloomfield, Conn., or from other sources. Other materials may also be suitable, such as materials plated with nickel or other conductive metals, or carbons.

Functioning of the Garment

When in use by the patient 16, for example by being attached to the garment 1, the flexible, electrically-conductive material 5 is in direct contact with the skin of the patent 16. Because of the low resistance of the flexible, electrically-conductive material 5, effective ion/electron transport across the material is provided, even at the low potentials typically present in the patient 16. The flexible, electrically-conductive material serves to create one or more current flow paths between points in the tissues of the patient 16 for electrical charges that naturally occur in the patient 16, as a result of normal biological processes.

The flexible, electrically-conductive material portions are typically applied to the skin of the patient 16 without using any conductivity enhancers such as pastes or cremes, though such enhancers may optionally be used as desired. The skin surfaces in contact with the flexible, electrically-conductive material portions are preferably clean and free from excessive hair, so as to provide improved conductivity. Hair present on the skin surfaces to be contacted may be removed by any of various conventional means, such as depilatory creams or shaving.

The flexible, electrically-conductive material portions, for example as attached to the garment 1, are preferably worn by the patient 16 for extended periods of time. For example, a daily period of use of 12 to 24 hours has been found to be effective, though as little as 4 hours a day will produce noticeable results. The garment 1 may be used for days, weeks, months or longer, until the desired results are obtained. The patient's body chemistry behaves as if they were engaging in long-term low-level exercise over an extended period of time. Fatty deposits within the patient 16 are reduced, giving way to denser, more muscular type tissue.

Over a period of time, the flexible, electrically-conductive material portions of the garment 1 being in direct contact with the skin of the patient 16 results in a reduction of available electrons in the fatty deposits proximal to the flexible, electrically-conductive material portions. The reduced amount of electrons in the fatty deposits, in relation to the electrical activity throughout the rest of the patient 16, where the flexible, electrically-conductive material portions are not present, causes the fatty deposits to be degenerated. This in turn causes a reduction in size of the fatty deposits. The reduction of the fatty deposits releases fat energy, stored as long chain molecules, into the blood stream as smaller, more easily metabolizable molecules that may be more readily converted into energy through normal biological processes of the patient 16.

In use, noticeable results can sometimes be seen after just a few days. Fatty deposits will be reduced in areas of the patient 16 in contact with the flexible, electrically-conductive material portions, and will not be reduced in areas not covered. For example, if the flexible, electrically-conductive material portions are in direct contact with fatty deposits on a first leg of the patient 16 and not a second leg of the patient 16, the first leg will become slim, and the second leg will not.

Additionally, use of the garment 1 will not cause the patient 16 to experience the hunger associated with many other forms of weight reduction. The fatty deposits broken down by the electrical activity triggered by the flexible, electrically-conductive material portions enter the bloodstream as smaller fat molecules. These molecules, suspended in the bloodstream, cause the patient 16 to feel as if the patient 16 had recently eaten. The patent 16 typically retains this feeling of satiation for as long as the patient 16 is wearing the garment i and there remains subcutaneous fatty deposits to be reduced by the action of the flexible, electrically-conductive material portions of the garment 1. The presence of the reduced fat, suspended in the bloodstream, stops hunger urges and digestive activity with essentially no fatigue or loss of energy. The usual sources of external caloric intake (food and drink) for the patient 16 are replaced by the reduced fat in the bloodstream. This reduction in the external caloric intake causes the patient 16 to experience weight loss.

Approximately one to three square feet of flexible, electrically-conductive material in direct contact with the fatty deposits of the patient 16 is sufficient to release enough fat to supply a normal basic daily caloric requirement. At night, to aid in sleeping, the garment 1 may be partially removed, flexible, electrically-conductive material portions within the garment 1 may be removed, or other garments having smaller flexible, electrically-conductive material portions may be worn.

Once weight loss begins to occur, the garment 1 should be worn as continuously as possible, preferably at least 16 hours per day. When the garment 1 is removed, the processes cease immediately, the fat molecules suspended in the bloodstream quickly re-bond to storage acceptor sites, and hunger begins. It may then take several hours or more, upon resumption of wearing the garment 1, for results to begin again.

The size measurement around the waist and thighs can drop a matter of several inches and many pounds in only a week or two of use. Once the desired weight and shape is obtained, if a reasonable diet is followed, the garment 1 may need be worn only zero or one or two days a month to maintain the shape.

Furthermore, since fatty tissues are reduced only under the flexible, electrically-conductive material portions of the garment 1, the garment 1 has the additional advantage in that it may be used to reduce certain body areas more than others, allowing the patient 16 to shape the body as desired by altering placement of the flexible, electrically-conductive material portions. In cases of large amounts of weight loss, several different sized garments may need to be used to accommodate the body as weight is lost and size is reduced. The device may be used by humans and mammals, and more generally by any living being that generates sufficient electrical charges within the body of the living being.

Details of Placement of Gaps and Electrically-Conductive Material Portions

The patient 16 has a naturally occurring potential gradient, created as a result of the normal biological processes occurring in the patient 16. This potential gradient runs generally from a high potential region located in the central portion 17 of the patient 16 radially outwards towards the extremities of the patient 16, such as the arm 24, head 20 and leg 21 shown in FIG. 4. Prolonged use of the garment 1 may cause undesirable side effects, due to the electrical activity triggered by flexible, electrically-conductive material portions interacting with the potential gradient. For example, nausea, gastric disturbances, severe cardiac disturbances, cardiac arrest, circulation impairment, cramping, central nervous system depression, loss of nerve sensitivity, and fatigue may occur. These side effects are substantially reduced or eliminated through careful placement of the flexible, electrically-conductive material portions, and use of insulating gaps, such as the gaps 14, 15 in the garment 1. The insulating gaps 14, 15 allow electrical charges to be shunted through the fatty deposits located proximal to the flexible, electrically-conductive material portions, yet preserve the overall potential gradient within the patient 16.

In contrast to the low resistance of the flexible, electrically-conductive material portions, the insulating gaps have a relatively high resistance, which substantially blocks current flow across the insulating gaps. The insulating gaps preserve the normal potential gradient between relatively distant portions of the patient 16, while allowing the flexible, electrically-conductive material portions to route current flow through portions of the patient 16 located near to each other. The insulating gaps create segregated treatment zones by placing a break around the flexible, electrically-conductive material portions, thereby dividing the flexible, electrically-conductive material into several electrically disconnected portions. For example, turning back to FIG. 2, the insulating gaps 14, 15 break the flexible, electrically-conductive material 5 into the separate flexible, electrically-conductive material portions 10, 11, 12, 13.

The insulating gaps 14, 15 need not be very large. A gap size of about 0.5 to 1 inch has been found to be sufficient to insulate the flexible, electrically-conductive material portions from each other. The insulating gaps 14, 15 allow each flexible, electrically-conductive material portion 10, 11, 12, 13 to be isolated and to stabilize at a slightly different electric potential, thus substantially preserving the potential gradient that naturally occurs in the patient 16. This prevents or substantially minimizes the undesirable side effects caused by disrupting the potential gradient.

Figure 4:
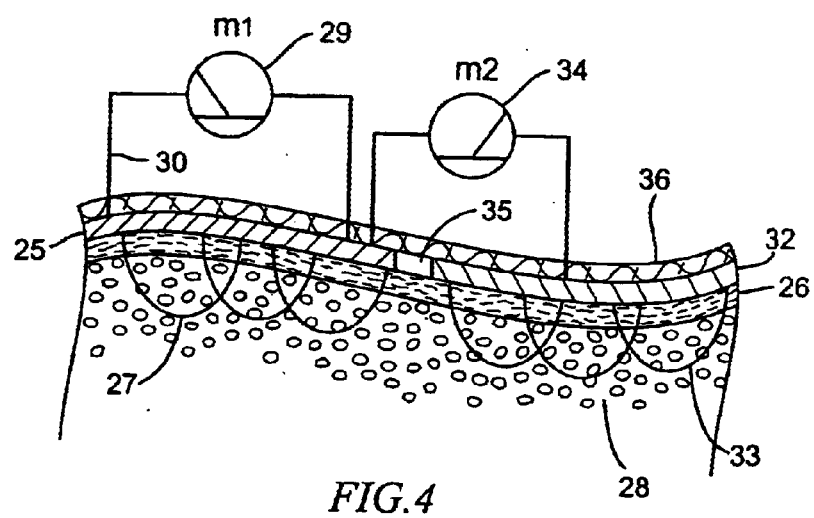
FIG. 4 shows a cross sectional view of the conductive portions as applied to the skin of a patient.

Turning to FIG. 4, the detailed operation of two flexible, electrically-conductive material portions 25, 32 are shown, including the effects of an insulating gap 35. A cross-sectional view of flexible, electrically-conductive material portions 25, 32 in direct contact with a skin surface 26 of the patient 16 is shown. A support portion 36 is attached to the flexible, electrically-conductive material portions 25, 32, to assist in keeping the flexible, electrically-conductive material portions 25, 32 in contact with the skin surface 26. Current paths 27 are formed across the surface of the flexible, electrically-conductive material portions 25, 32 and through the fatty deposit 28, where the flexible, electrically-conductive material portions 25, 32 cover the skin surface 26. A first milli-voltmeter 29 is connected across a first extent 30 between two points both on the surface of the flexible, electrically-conductive material portion 25. This first milli-voltmeter shows very little voltage across the extent 30, since the endpoints of the first extent 30 are attached to the same flexible, electrically-conductive material portion 25. A second milli-voltmeter 34 is connected across a second extent 31 between a point on the surface of the flexible, electrically-conductive material portion 25 and a second point on the surface of the flexible, electrically-conductive material portion 32, across the insulating gap 35. The second milli-voltmeter 34 shows a voltage potential between the flexible, electrically-conductive material portions 25, 32. The insulating gap 35 allows each of the flexible, electrically-conductive material portions 25, 32 to maintain a potential independent of each other, and of any other flexible, electrically-conductive material portions in contact with the patient 16. This causes a shunt current to flow through the fatty deposit 28 proximal to each flexible, electrically-conductive material portion 25, 32, but prevents disturbance of the overall potential gradient present in the patient 16.

When the flexible, electrically-conductive material portions 25, 32 are mounted to a garment, such as the garment 1 discussed above, a support portion 36 may be added to the garment 1 to facilitate operation of the flexible, electrically-conductive material portions 25, 32. The support portion 36 is generally constructed of a relatively high resistance flexible material, substantially higher in resistance than the flexible, electrically-conductive material portions 25, 32. The support portion 36 preferably has a resistance of greater than 100,000 ohms per square inch, and particularly preferably has a resistance of 1,000,000 ohms per square inch. Typical clothing materials such as cotton, polyester, Spandex™, etc., are suitable for use in the support portion 36. The support portion 36 also provides structural support to the garment 1, to hold the flexible, electrically-conductive material portions 25, 32 in direct contact with the skin surface 26 of the patient 16.

Undesirable side effects are also mitigated or avoided through proper location of the flexible, electrically-conductive material portions with respect to the various components of the patient 16, such as internal organs, fatty deposits, bones and bone joints, etc. The flexible, electrically-conductive material portions are preferably placed only proximal to significant subcutaneous fatty deposits. A simple test to detect the presence of sufficient fatty deposits exists. If more than approximately one inch thickness of fatty skin on the patient 16 can be grasped in a single pinch, then there may be adequate fat present in the treatment area of the patient 16.

The flexible, electrically-conductive material portions are preferably not placed proximal to bones in the patient 16. The flexible, electrically-conductive material portions are preferably placed no closer than about 0.5 to 1 inch away from any significant bone mass. The flexible, electrically-conductive material portions are preferably not placed on the back, shoulders, spinal column, or ribcage of the patient 16, as such use may cause undesirable disturbances in the normal body functions of the patient 16. The flexible, electrically-conductive material portions are preferably not placed within 0.5 to 1 inch of any large blood vessels or arteries, unless those blood vessels are covered by a fatty deposit. At least one insulating gap should be located along the dominant axis of larger flexible, electrically-conductive material portions contacting the patient 16.

Additionally, there are various bio-electrical circuits which exist within the patient 16. Various bio-electrical circuits are found to exist in the body. These circuits are involved in various processes. Some of the circuits are closed loop, and operate with feedback mechanisms. Some circuits involve the bones, others involve the blood and nerves. A single flexible, electrically-conductive material portion should not be placed along the entire length of one of these circuits within the patient 16. For example, a single flexible, electrically-conductive material portion should not be placed along the entire length of the arm 24 or leg 21. A single flexible, electrically-conductive material portion placed in this manner and crossing bone joints can result in depression of nerve sensation and the central nervous system in the arm 24 or leg 21 and should be avoided. It is found that when a single flexible, electrically-conductive material portion transverses a bone joint, undesirable disruption of electrical processes occur, and degeneration of joint tissue may occur. Thus, in the preferred embodiment, there is a insulating break in the flexible, electrically-conductive material portion over the area of each bone joint.

In addition, certain zones or areas of the patient 16 should preferably be segregated, even when fatty deposits exist. A flexible, electrically-conductive material portion contacting the stomach/abdomen should be unconnected to other flexible, electrically-conductive material portions, and should not extend all the way around the waist and the back half of the patient 16. Flexible, electrically-conductive material portions covering the inner thigh, outer thigh, and buttocks should have insulating gaps between them. An insulating gap may be placed approximately every 6 to 18 inches of coverage, as measured outwards radially from the central portion 17 of the patient 16, to obtain effective results while minimizing undesired reactions. When the above guidelines regarding placement are followed, it is found the garment 1 may be used for days, weeks, or months, until the desired results are obtained.

The female chest area may be treated if the conductive portion is kept at least about 1 inch away from the central portion 17 of the patient 16. Such application may be used in place of chest reduction surgery.

In alternate embodiments, the flexible, electrically-conductive material portion can be applied as an electrically conductive ink or paint, by brushing or painting such materials onto the skin of the user or inside the garment 1 to form the electrically conductive material portion, as well as other techniques of manufacturing the conductive portions, including use of various low resistance metal and carbon powders and fibers. The support portion can also be mixed in with the electrically conductive ink or paint, such as a glue or other fixing or bonding agent. This mixture can then be applied to the skin of the patient.

The garment 1 may be manufactured, packaged marketed and sold as a weight loss device or garment for the reduction of fatty deposits. It may also be marketed as a body shaping device. The garment 1 may be labeled to "lose weight", "burn fat", "trim size", "diet aid", "thigh buster" or the like to indicate its use. It may be sold in stores, through distributors, malls, by mail order, the Internet, television, or other means, and may include instructions and warnings for use as a weight loss, body shaping or other such device. The garment 1 may also be sold or marketed as a natural "muscle builder", "shaper", "toner" or the like. Constructing the garment 1 in this manner will allow most people to wear and use the garment 1 comfortably, and without harmful effects.

Thus embodiments of the disclosed apparatus provide a novel means of reducing undesirable fatty deposits and losing weight that is both safe and convenient to use, doesn't require physical exertion, and provides effective results. In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than restrictive sense, and the invention is not to be restricted or limited except in accordance with the following claims and their legal equivalents.

I claim:

1. A method for weight reduction in a patient, comprising:
   locating a subcutaneous fatty deposit in the patient;
   identifying a first skin surface, proximal to the subcutaneous fatty deposit;
   creating a current flow path for an electric charge naturally present in the patient;
   maintaining the current flow path for a time period sufficient to cause significant electrically-triggered weight reduction.

2. The method of claim 1, wherein creating a current flow path comprises applying a low-resistance electrically conductive material directly to the first skin surface.

3. The method of claim 2, wherein maintaining the current flow path comprises maintaining the low-resistance electrically conductive material in contact with the first skin surface.

4. The method of claim 1, further comprising identifying a second skin surface, the second skin surface not being proximal to the fatty deposit, and avoiding application of the low-resistance electrically conductive material to the second skin surface.

5. The method of claim 4, wherein the second skin surface is proximal to a bone joint.

6. The method of claim 1, wherein the time period comprises at least four hours per day for at least three days.

7. The method of claim 1, further comprising depilatating the first skin surface.

8. The method of claim 1, further comprising applying a conductivity enhancer to the first skin surface.

9. The method of claim 1, further comprising removing the low-resistance electrically conductive material once the fatty deposit subsides.

10. A garment for reducing weight in a patient, comprising:
a low-resistance electrically conductive material portion adapted to directly contact a first skin surface of the patient, the first skin surface being proximal to a fatty deposit in the patient; and
a support portion adapted to maintain the low-resistance electrically conductive material portion in direct contact with the first skin surfaces 1
wherein the low-resistance electrically conductive material portion is adapted to conduct an electric charge naturally occurring in the patient.

11. The garment of claim 10, wherein the support portion comprises an electrically insulating material.

12. The garment of claim 11, wherein the support portion is adapted to minimize disruption of a potential gradient running from a central portion of the patient to an extremity of the patient.

13. The garment of claim 11, wherein the low-resistance electrically conductive material portion comprises one or more low-resistance electrically conductive material portions, wherein the support portion is adapted to electrically insulate the one or more low-resistance electrically conductive material portions from each other.

14. The garment of claim 13, wherein the one or more low-resistance electrically conductive material portions are located substantially proximal to one or more fatty deposits in the patient.

15. The garment of claim 13, wherein the support portion comprises a plurality of gaps between the one or more low-resistance electrically conductive material portions.

16. The garment of claim 14, wherein the gaps are about 0.5 to 1 inch wide.

17. The garment of claim 14, wherein the gaps are located approximately every 6 to 18 inches, measured outwards radially from a central portion of the patient towards an extremity of the patient.

18. The garment of claim 14, wherein one or more of the gaps is located substantially proximal to a bone joint.

19. The garment of claim 10, wherein the low-resistance electrically conductive material comprises a resistance less than about 10,000 ohms per square inch.

20. The garment of claim 10, wherein the low-resistance electrically conductive material is attached to the support portion with user-adjustable fasteners.

21. The garment of claim 10, wherein the low-resistance electrically conductive material comprises a flexible cloth-like material.

22. The garment of claim 21, wherein the cloth-like material comprises silver-plated woven nylon cloth.

23. The garment of claim 10, wherein the low-resistance electrically conductive material portion is sufficiently large enough to shunt enough of a naturally occurring potential gradient in the patient to trigger substantial weight reduction in the patent.

24. The garment of claim 10, wherein the garment is adapted to create a current flow path for an electric charge in the patient.

25. The garment of claim 10, wherein the garment is adapted to maintain the current flow path for a time period sufficient to cause significant electrically-triggered weight reduction.

26. The garment of claim 10, wherein the patient further comprises a second skin surface, the second skin surface not being proximal to the fatty deposit, and wherein the garment is adapted to avoid application of the low-resistance electrically conductive material to the second skin surface.

27. The garment of claim 10, wherein the garment comprises a liquid, adapted to be applied to the first skin surface.

28. The garment of claim 27, wherein the low-resistance electrically conductive material portion comprises a paint.

29. The garment of claim 27, wherein the support portion comprises a fixing agent.

30. The garment of claim 29, wherein the fixing agent is mixed with the low-resistance electrically conductive material portion and the combination is applied to the first skin surface.

* * * * *